United States Patent
Thonhauser

(10) Patent No.: US 8,493,441 B2
(45) Date of Patent: Jul. 23, 2013

(54) ABSORBANCE MEASUREMENTS USING PORTABLE ELECTRONIC DEVICES WITH BUILT-IN CAMERA

(75) Inventor: Christian Thonhauser, Vienna (AT)

(73) Assignee: Thonhauser GmbH, Perchtoldsdorf (AT)

( * ) Notice: Subject to any disclaimer, the term of this patent is extended or adjusted under 35 U.S.C. 154(b) by 821 days.

(21) Appl. No.: 12/558,442

(22) Filed: Sep. 11, 2009

(65) Prior Publication Data

US 2011/0063433 A1    Mar. 17, 2011

(51) Int. Cl.
*G01N 21/78* (2006.01)

(52) U.S. Cl.
USPC .......................................... 348/135; 348/336

(58) Field of Classification Search
USPC .................................... 382/163; 348/135, 336
See application file for complete search history.

(56) References Cited

U.S. PATENT DOCUMENTS

| | | | | |
|---|---|---|---|---|
| 5,272,518 A * | 12/1993 | Vincent | ......................... | 356/405 |
| 7,761,079 B2 * | 7/2010 | Mollenkopf et al. | ......... | 455/402 |
| 7,804,763 B2 * | 9/2010 | Berkman et al. | ............. | 370/208 |
| 7,948,392 B2 * | 5/2011 | Smith et al. | ................ | 340/693.6 |
| 2006/0092182 A1 * | 5/2006 | Diefenbaugh et al. | ........ | 345/690 |
| 2006/0222567 A1 | 10/2006 | Kloepfer et al. | | |
| 2006/0292039 A1 | 12/2006 | Iida | | |
| 2009/0220148 A1 * | 9/2009 | Levy et al. | ..................... | 382/163 |
| 2012/0309636 A1 * | 12/2012 | Gibbons et al. | ................... | 506/9 |

FOREIGN PATENT DOCUMENTS

| | | |
|---|---|---|
| EP | 1801568 A1 | 6/2007 |
| JP | 2005236470 A | 9/2005 |
| WO | 2006/127840 A2 | 11/2006 |

OTHER PUBLICATIONS

European Search Report in related application EP 10 17 6227 mailed Dec. 23, 2010.

* cited by examiner

*Primary Examiner* — Khanh Dinh
(74) *Attorney, Agent, or Firm* — Pillsbury Winthrop Shaw Pittman LLP

(57) ABSTRACT

A method comprising obtaining a mobile electronic device comprising a color sensitive light sensor and outward facing optics, exposing a sample to light having a predetermined optical path-length between a light source and the color sensitive light-sensor, and measuring the amount of light transmitted though the sample with the color sensitive light sensor. Also a mobile electronic device comprising a color sensitive light sensor and outward facing optics, the mobile electronic device configured for quantitative analysis of absorbance in colored liquids. Additionally, a system comprising a mobile electronic device configured for quantitative analysis of absorbance in colored samples, the mobile electronic device comprising a color sensitive light sensor and outward facing optics and a light source.

55 Claims, 5 Drawing Sheets

ABSORBANCE MEASUREMENTS USING PORTABLE ELECTRONIC DEVICES WITH BUILT-IN CAMERA

FIELD OF THE INVENTION

The present invention relates to absorbance detectors, and more in particular to portable absorbance detectors with built in cameras.

BACKGROUND OF THE INVENTION

The Beer-Lambert law, also known as Beer's law relates the absorption of light to the properties of the material through which the light is traveling. The law states that there is a logarithmic dependence between the transmission (or transmissivity), T, of light through a substance and the product of the absorption coefficient of the substance, $\alpha$ ($\alpha'$), and the distance the light travels through the material (i.e. the path length), l. The absorption coefficient can, in turn, be written as a product of either a molar absorptivity (extinction coefficient) of the absorber, $\epsilon$, and the concentration c of absorbing species in the material, or an absorption cross section, $\sigma$, and the (number) density N of absorbers.

For liquids, these relations are usually written as $$T = \frac{I}{I_0} = 10^{-\alpha l} = 10^{-\epsilon l c}$$

whereas for gases, and in particular among physicists and for spectroscopy and spectrophotometry, they are normally written $$T = \frac{I}{I_0} = 10^{-\alpha' l} = 10^{-\sigma l c}$$

where $I_0$ and $I$ are the intensity (or power) of the incident light and the light after passing through the material, respectively. The transmission (or transmissivity) is expressed in terms of an absorbance which for liquids is defined as $$A = -\log_{10}\left(\frac{I}{I_0}\right)$$

whereas for gases, it is usually defined as $$A' = -\ln\left(\frac{I}{I_0}\right)$$

This implies that the absorbance becomes linear with the concentration (or number density of absorbers) according to A=$\epsilon$lc=$\alpha$l and A=$\sigma$lN=$\alpha'$l for the two cases, respectively.

Thus, if the path length and the molar absorptivity (or the absorption cross section) are known and the absorbance is measured, the concentration of the substance (or the number density of absorbers) can be deduced.

A conventional photometer is schematically illustrated in FIG. 1. The conventional photometer includes a light source $1a$, a device for generating monochromatic light $2a$, a liquid target $3a$, a light sensor $4a$, and a display $5a$. The light source $1a$, device for generating monochromatic light $2a$, liquid target $3a$, and light sensor $4a$ are contained within a housing $6a$. The display $5a$ is typically located on an outside surface of the housing $6a$. The monochromatic light generally has a spectral bandwidth usually between 0.5 and 10 nm. The device may be a prism, an optical grating or a colour filter (low band-width interference filters or colour filters). This monochromator device can be located either in front or behind the liquid target. The light beam of the conventional photometer is generated by an optical system (lenses or mirrors) from an omnidirectional light source. Typically, the light sensor (e.g. a photo-diode or a photo-multiplier-tube) of the conventional photometer is not capable of distinguishing various colours. More recent devices use multi-CCD (line) detectors, however, the various wavelengths still have to be spatially separated by passing the light-beam through a grating or prism before entering the detector.

The conventional photometer is entirely housed in a single housing $6a$. Because of the construction of the conventional photometer, the optics are inward facing. That is, the optics are configured to look within the apparatus toward central chamber in which the sample is placed.

SUMMARY OF THE INVENTION

An embodiment of the present invention includes a method comprising obtaining a mobile electronic device comprising a color sensitive light sensor and outward facing optics, exposing a sample to light, and measuring the amount of light transmitted though a predetermined optical path-length in the sample with the color sensitive light sensor, wherein the sample and the mobile electronic device are not enclosed within the same housing. In one aspect, the method further comprises determining the light absorption of the sample by wavelength-extraction from red, green and blue colors. In another aspect, the method further comprises calculating the mass or molar concentrations of a substance in the sample.

Another aspect further comprises adding a color indicating reagent to the sample. Another aspect further comprises adding a reagent of unknown concentration to the sample, the sample comprising a color indicating agent. In another aspect, the color indicating reagent is selected from redox, acid-base and complexation. In another aspect, the color indicating reagent is selected from redox, acid-base and complexation. In another aspect, the color sensitive light sensor is part of a digital camera. In another aspect, the mobile electronic device comprises a backlit display and the backlit display is used as the light source.

In another aspect, the backlit display is used discontinuously by selectively displaying discrete colors for a predetermined amount of time. In another aspect, the discrete colors are complementary to absorption maxima of a substance in the sample. Another aspect further comprises channeling light from the backlit display though the sample and to the outward facing optics with an optical fiber. In another aspect, the color sensitive light sensor is illuminated uniformly by the light source. In another aspect, the mobile electronic device uses 8-bit color processing. In another aspect, the light source comprises a source of white light and a source of ultraviolet light.

Another aspect further comprises putting the sample in a container having parallel walls. In another aspect, the device comprises voice control. Another aspect further comprising measuring the amount of light transmitted though a reference. In another aspect, the reference has essentially 100% transmittance. In another aspect, if the mobile electronic device has automatic exposure, the automatic exposure is turned off. In another aspect, a captured image from the color sensitive light sensor is cropped in a predetermined configuration. Another aspect further comprises determining average values for red, green, and blue light levels.

In another aspect, the device is configured to capture an image. Another aspect further comprising using a reference transmittance of 100% if no reference transmittance has been measured. In another aspect, the mobile electronic device and/or the light source are immersed in the sample. In another aspect, the light source is selected from fluorescent and light emitting diode.

Another embodiment relates to a mobile electronic device comprising a color sensitive light sensor, a processor, and outward facing optics, the processor comprising computer executable instructions for quantitative analysis of absorbance in colored liquids. One aspect further comprises a visual or acoustic user interface. In another aspect, the device is configured for quantitative analysis of absorbance in colored liquids with software. In another aspect, the device is configured for quantitative analysis of absorbance in colored liquids with hardware. In another aspect, the light sensor is a digital camera. In another aspect, the device comprises hardware and firmware and/or software and wherein at least one of the hardware, firmware and software is user-programmable.

Another aspect further comprises a user interface comprising a dot-matrix display. Another aspect further comprises a user interface comprising a touch-sensitive display. In another aspect, the device is configured to calculate the mean red, green and blue color levels from predetermined portions of the digital image. In another aspect, the device is configured to calculate liquid absorbances based on wavelength-extraction of red, green and blue color levels. In another aspect, the device is configured to calculate mass or molar concentrations of a substance external to the liquid, further. In another aspect, the liquid is reactive towards the substance and changes colors upon contact with the substance.

Another aspect further comprises a backlit display configured for use as light source. In another aspect, the device is configure to display multiple colors in succession and respective light-sensor intensities are captured. In another aspect, the digital camera is configured to operate in video mode. In another aspect, the device is configured to monitor a change in color as a function of time.

Another embodiment relates to a system comprising a mobile electronic device comprising a color sensitive light sensor, a processor, and outward facing optics, the processor comprising computer executable instructions for quantitative analysis of absorbance in colored samples, and a light source. One aspect further comprises a fixed optical path length for the colored sample. Another aspect further comprises a fluorescent lamp as light source. Another aspect further comprising a user interface physically built into the mobile device. In another aspect, the mobile electronic device comprises a backlit display configured for use as light source. Another aspect further comprises an optical fiber configured to transmit light from the backlit display to a sample.

Another aspect further comprising an optical fiber configured to transmit light from the sample to the color sensitive light sensor. In another aspect, the mobile electronic device is configured to determine light absorption of the sample based on wavelength-extraction from red, green and blue colors. In another aspect, the mobile electronic device is configured to calculate the mass or molar concentrations of a substance in a sample. In another aspect, the color sensitive light sensor is part of a digital camera. In another aspect, the mobile electronic device is configured to use 8-bit color processing. Another aspect, further comprises a sample and a blank. In another aspect, the sample is selected from liquids, gases, gels, and semi-transparent solids.

BRIEF DESCRIPTION OF THE DRAWINGS

The novel features that are considered characteristic of the invention are set forth with particularity in the appended claims. The invention itself; however, both as to its structure and operation together with the additional objects and advantages thereof are best understood through the following description of the preferred embodiment of the present invention when read in conjunction with the accompanying drawings, wherein:

DETAILED DESCRIPTION

Figure 1:
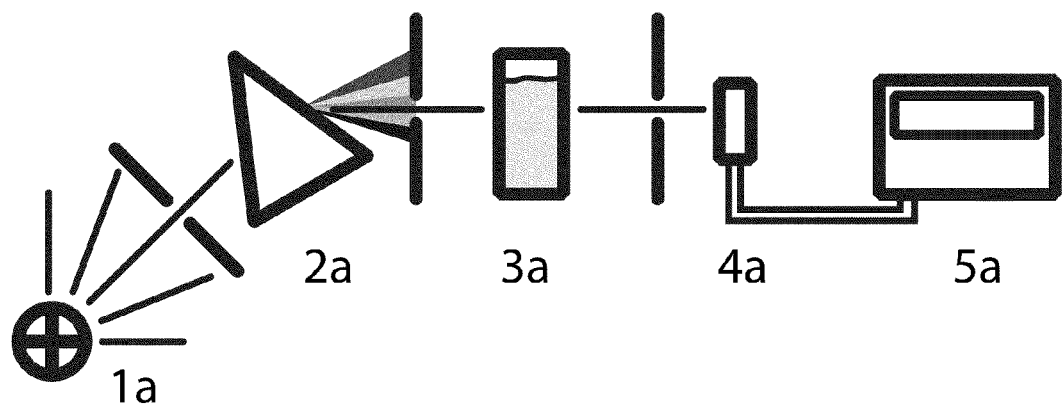
FIG. 1 is a schematic view of a conventional photometer configuration.
Figure 2:
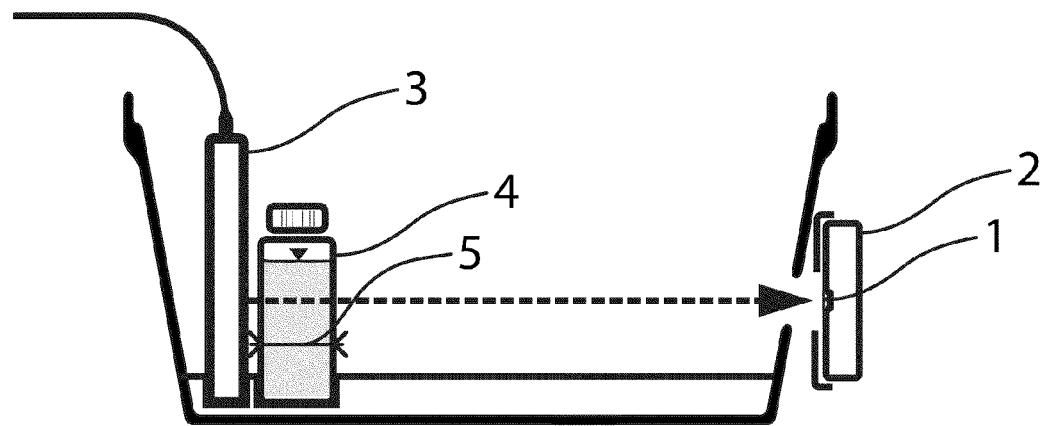
FIG. 2 is a schematic view of a device according to an embodiment of the invention.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In this application, "inward facing optics" means that the optics are configured to look within the apparatus. That is, toward a central chamber (within the housing of the apparatus) in which the sample is placed. "Outward facing optics" means the optics, typically of a portable electronic device, point out from the portable electronic device. That is, outwardly facing optics are configured to record light intensities and/or images from the surroundings of the mobile device.

A "mobile electronic device" is a device that is designed to be used in different locations typically for short periods of time (minutes to hours). Mobile electronic devices are often equipped with a power supply that does not rely on the availability of main power.

Light absorption determined by "wavelength extraction" means determining the light absorption by calculating wavelength-specific light transmittances extracted mathematically from the recorded red, green and blue colours and further applying logarithmic comparison with unattenuated light intensity.

A "colour indicating reagent" is a substance that is configured to react with external substances to yield differently coloured species.

Generally, the light sensor does not need to be sensitive towards particular colours if discrete colours are used for illumination of the sample. This is especially true when using a thin film transistor (TFT) display as a sequential, multi-colour light source.

A "discrete colour," when using three primary colours (RGB), is defined by three single levels/numbers for red, green and blue, wherein the numbers must lie within the range defined by the bit-resolution available.

"Complementary colors" are pairs of colors that are of "opposite" hue in some color model. Within the RGB model, complementary colours are calculated by subtraction of the individual R, G and B levels from the maximum levels defined by the bit-resolution.

The "average value" for individual R, G, and B levels are calculated by addition of the individual R, G and B levels for each pixel and dividing by the number of pixels evaluated. (=arithmetic mean). The results are single values for each of R, G and B. The average colour of the pixels is thus evaluated.

A "predetermined optical path-length" means the distance the light travels through the colored sample. For accurate calculation of the absorbance, the optical path-length should be accurately measured. The placement of the light source and the color sensor is irrelevant to the optical path-length.

Rapid technological progress has made portable electronic devices with built-in still or movie cameras widely available. The quality of cameras has improved significantly over the last years, despite the small sensor sizes used in low-profile handheld electronics. If light intensity is reasonably high, the CCD (charge coupled device) or CMOS (Complementary Metal Oxide Semiconductor) sensors deliver images that are hardly affected by sensor noise and compression and/or sensor interpolation artefacts.

The inventor has discovered that coloured liquids that absorb light in the visible part of the spectrum (as well as in adherent near ultraviolet and near infrared ranges) can be characterised and quantitatively analysed by these cameras with reasonable precision. To achieve a suitable precision, several parameters may be adjusted. These factors include, for example, (1) a balance between transmitted light intensity and optical path-length, (2) providing sufficient light intensity at wavelengths finally extracted from the RGB (red-green-blue) image data over the absorbance spectrum of a given substance, (3) illuminating the usable part of the camera image uniformly and (4) reliable camera control/camera behaviour.

The balance between transmitted light intensity and the optical path length should be struck to provide sufficient intensity of transmitted light. The balance is a function of both the concentration of the coloured substance and substance-specific absorbance. For example, for a sample having a high concentration of a substance with a high substance-specific absorbance (extinction coefficient), a short optical path length should be used. For low concentrations and compounds having low substance-specific absorbance, a long optical path may be used.

Preferably, the light source(s) should provide sufficient light intensity at all wavelengths finally extracted from the RGB (red-green-blue) image data over the absorbance spectrum of a given substance to distinguish over noise. When adjusting the analytical system, it is advisable to carefully observe light-sensor noise levels, particularly when analysing liquids that contain coloured species in high concentration ranges and/or with high molar extinction coefficients. As discussed above, high concentration ranges and high molar extinction coefficients lead to a significant loss of light intensity by molecular absorption.

Data with current sensor types shows that bit-modulation below approximately 20 levels (of 256 possible 8-bit levels) is adverse for analytical precision. This is because with current sensors sensor noise cannot be reduced sufficiently and colour rendition starts to become poor below that value.

Sufficient light intensity can be achieved by varying system parameters. For example, light intensity (increase), optical path-length (decrease), and sensor amplification (expressed in digital imaging as "ISO-sensitivity") can be varied over a wide range. Note, however, that the light intensity received by the sensor should not reach or exceed the maximum saturation/dynamic range of the sensor. Additionally, the light intensity is usually further limited by the maximum modulation of the bit-resolution (at the time of the invention generally 8-bits/channel).

Additionally, the light source(s) should illuminate the camera image uniformly. More specifically, the light source(s) should uniformly illuminate the portions of the image which being used for colour analysis. As discussed in more detail below, it is not necessary to use the entire sensor area of a camera. In some embodiments, only a portion of the sensor area is used. "Uniform lighting" can be expressed as a lack of induced differences in RGB levels within the selected colour crop area. It is preferable to get final wavelength-specific absorbance results with a standard deviation of less than 5%, when selecting various sub-ranges from the pre-defined crop area. A selected sub-range should contain a significant amount of pixels, generally more than 100 (10×10 Pixel square).

Preferably, the camera control/camera behaviour should be reliable. Reliability can be characterised in terms of white balance, exposure control and in-device post-processing. Exposure control precision can be derived from repeatability between multiple exposures of the same coloured liquid, both for intra- (same device) and inter- (different devices of same make and model) device conditions. It is preferable to observe variations of less than 5 8-bit levels for all three individual RGB colour channels for intra-device repeatability and less than 10 8-bit levels for various specimen of the same device. Post-processing includes the imaging process steps to get a colour image from the read-out CCD or CMOS photosite intensities. Example post-processing processes include applying noise-filtering, BAYER-interpolation and JPEG compression algorithms to the original intensities. Reliability may be implemented by means of direct hardware related programming or in form of out-of-the-box solutions provided by the manufacturer.

With proper selection of process parameters, the quality of absorbance measurement with current camera sensors can meet or even exceed the data quality provided by conventional industrial photometrical devices (e.g. filter, dispersive or photosensor-array spectrometers). Indeed, data shows that the current camera limitation of having only 8-bit (256 levels) per colour channel available for data processing has proven to be largely insignificant for the quality of the final analysis data.

If actual absorbances and therefore concentrations are desirable, it is preferable to establish both a constant light output from the light source as well as constant exposure bias. Thus, it is preferable not to use automatic exposure. Automatic exposure generally results in images with a standard grey value of 18%, which is equal to 130 8-bit RGB levels regardless of the actual colour and illumination of the thing being photographed. That is, samples having similar but different colours taken under automatic exposure will tend to have the same image colour.

Constant exposure bias can be maintained by balancing the parameters: sensor ISO-sensitivity, f-stop (aperture) and exposure (shutter) time. For example, if the exposure time is increased by a factor of 2, either the aperture has to be further stopped down by one f-stop or the ISO-sensitivity has to be reduced by one EV ("exposure value"), e.g. from ISO 200 to ISO 100.

In another embodiment, automatic exposure can be used. In this embodiment, the limitations for concentration-dependent absorbance analysis caused by the automatic exposure control of in-device cameras can be compensated for by using the camera metadata. This metadata is typically stored together with the actual image (e.g. the common EXIF data, "Exchangeable Image File Format"). For example, the most recent SYMBIAN S60 3rd Edition devices already record ISO sensitivity, f-stop and exposure time. With this data, the actual colour, and thus, the sample concentration can be calculated.

The metadata can be used for compensating the tendency of automatic exposure to generate an image with an average 18% standard grey value by observing the geometric progression of the three exposure-relevant values (ISO sensitivity, f-stop and exposure time) and performing a gamma-correction based on the originally read-out RGB levels. The resulting, compensated RGB levels are then suitable for quantitative determination of actual absorbances or even concentration levels of coloured liquids/dissolved species.

In an alternative embodiment, an adjustment based on current draw can be included. In this embodiment, of the transmitted light depending on the intensity of the RGB signal recorded by the camera and using the actual light-amplification, e.g. in form of LED (light emitting diode) current draw, in the calculation algorithm. This method helps to overcome the sub-optimal dynamic range of small sensors, that are even more confined by the subsequent 8-bit image processing. The analysis of liquids with high absorbance and/or long optical path-length becomes possible by using this method.

Embodiments of devices and systems are illustrated in FIGS. 2-5. The embodiment illustrated in FIG. 2 includes a sensor 1 in a portable electronic device 2. This embodiment also includes a colour solution 4 in a container having a defined path-length 5. On the opposite side of the colour solution 4 from the sensor 1 is a light source 3. In contrast to the convention photometer, the portable electronic device 2 of the system illustrated in FIG. 2 has outward facing optics. That is, the optics of the portable electronic device 2 point out from the portable electronic device 2.

Figure 3:
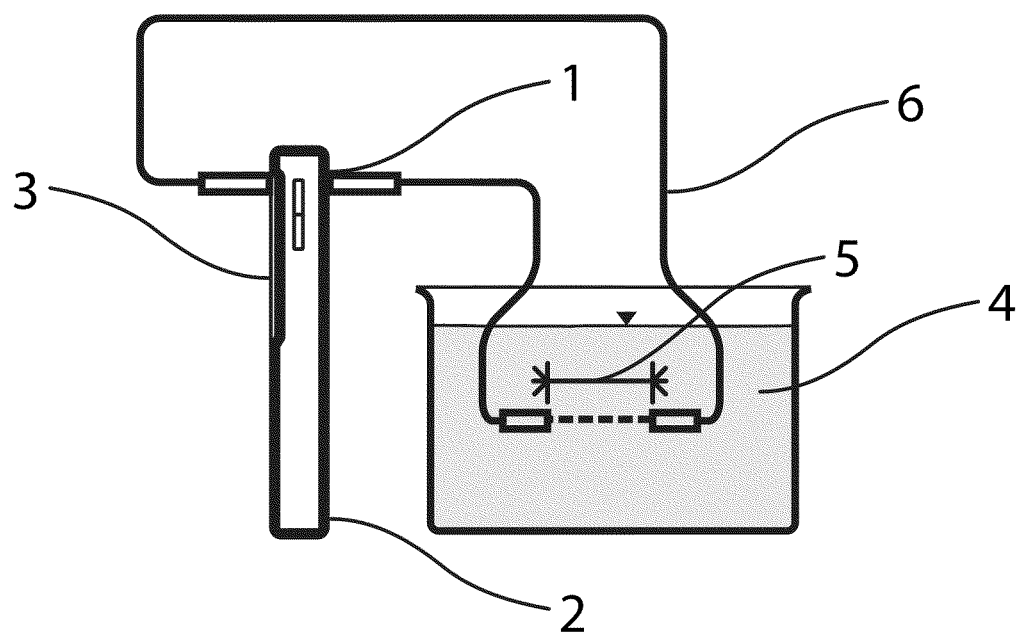
FIG. 3 is a schematic view of device according to another embodiment of the invention.
Figure 4:
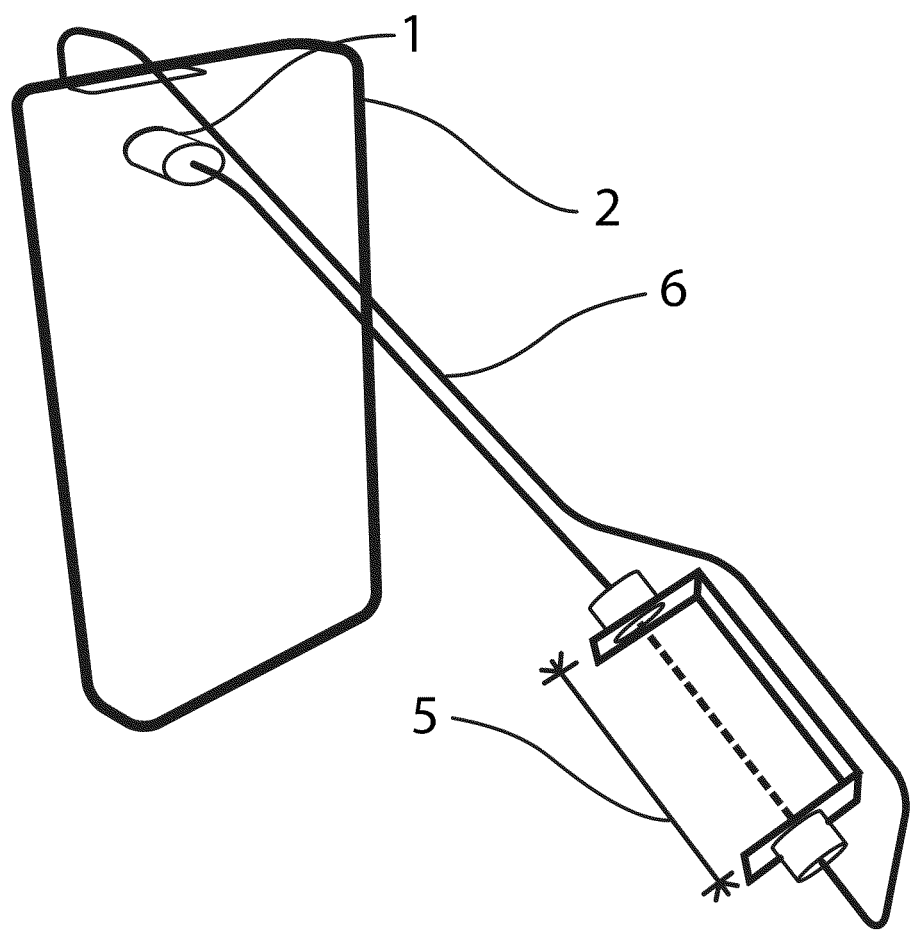
FIG. 4 is a perspective if the embodiment illustrated in FIG. 3.
Figure 5:
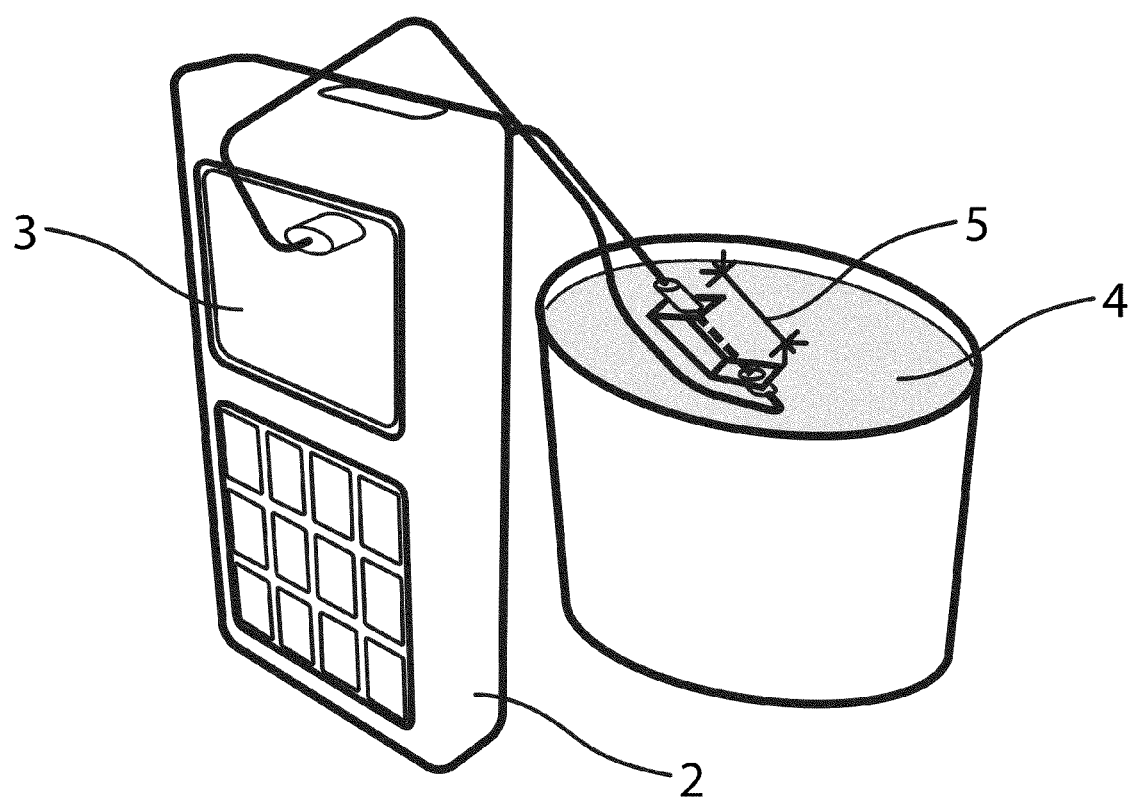
FIG. 5 is another perspective if the embodiment illustrated in FIG. 3.

FIGS. 3-5 illustrate another embodiment of the invention. This embodiment includes a sensor 1 in a portable electronic device 2. Unlike the previous embodiment, the portable electronic device 2 of this embodiment also includes a light source 3. The system also includes an optical fiber 6 that runs from the light source to the solution 4. Spaced apart in the solution by a defined path-length 5 is a second optical fiber 6 which runs from the solution 4 to the optical sensor 1. Unlike the embodiment illustrated in FIG. 2, the present embodiment need not have a container having a with a defined path-length. The ends of the optical fiber 6 may be held spaced apart with a bracket as illustrated in FIG. 4 or any other suitable structure. Additionally, as illustrated in FIG. 5, the portable electronic device 2 may be a cell phone, a personal digital assistants, or similar devices. Preferably, the portable electronic device 2 is programmable by the user, however, this is not necessary. Programming options are discussed in more detail below.

Light Source:

Tests were conducted using tungsten, white LED and fluorescent light sources. All of these light sources are suitable for the method described and provide a reasonable light intensity for absorbance spectra in the range of 400-700 nm. White LED's, however are generally not suitable for analysing absorbances below ca. 450 nm. For analysis at wavelengths below 450 nm, a UV LED with a maximum intensity at 400-405 nm may be used.

In an alternative embodiment, the use of the device display itself (together with the backlight) can be used and allows generation of multiple complementary colours. The multiple complementary colours may be selected based on the coloured species to be analysed. That is, the wavelength of the transmitted light may be optimized for the species to be analysed. Separate images for each light colour may be recorded.

Liquid Target:

If an immersion technique is not used (see section "Modifications of method"), use of a rectangular shaped glass or transparent plastic (e.g. polystyrene, polycarbonate, poly(methyl methacrylate)) container ("cuvette") may be advantageous. A rectangular (or square) container provides a uniform optical path-length for all parts of the image recorded. Moreover, the parallel glass side-walls minimise light reflections and therefore reduce over-modulation of certain parts of the image. An optical path-length of approximately 10-80 mm (0.4-3.1 inches) has be proven to be appropriate for most coloured solutions.

Devices:

Devices useable for the method described include a digital camera or another, colour photodetectors. Preferably, the devices include a visual or at least a bidirectional acoustic user interface. In one embodiment, the display is a dot-matrix. In other embodiments, the display comprises a high-resolution, backlit TFT (thin film transistor) display. Both external controls (buttons, multi-controllers, wheels) or touch sensitive displays are suitable for image capture and software control. Alternatively, voice control and voice output may be used.

Preferably, the device selected is user-programmable in a way that certain hardware parts of the device and operating system/software/firmware functions can be addressed, executed and adjusted. In one embodiment, this may accomplished with by custom-made software. The custom-made software may be deployed, for example, by downloading and installing. Alternatively, software may be installed by the device or operating system manufacturer. In another alternative embodiment, an commercially available digital camera (or its equivalent) may be modified by the physical replacement of electronic parts of the device with equivalent parts modified to perform the method.

Currently several mobile operating systems support custom software. Examples include Mobile UNIX distributions, such as NOKIA SYMBIAN S60, and GOOGLE ANDROID. Other devices use proprietary operating systems. Examples include, APPLE IPHONE/POD TOUCH OS, WINDOWS MOBILE/CE, and PALM OS).

At the current time, mobile phones, certain portable music-players and PDA's (personal digital assistants) as well as low-profile notebook computers are suitable devices. Cameras (still and movie) or multifunctional navigation systems may also be used. Of course, the custom-design devices for use within the scope of the invention may also be used.

General Set-Up for Quantitative Analysis of Absorbance of Liquids:

For an accurate measurement of absorbance (also referred to as "optical density"), the recording of 100% transmittance (0% absorbance, $I_0$) is preferable. This can be seen from the underlying Beer-Lambert law (absorbance=$-\log_{10}(I/I_0)$), where I is the wavelength-specific light intensity recorded by the detection system.

Comprehensive testing has revealed, that there is no need to record $I_0$ prior to each absorbance measurement, if The light source has a constant output.

The optical path-length remains constant.

The camera exposure bias is not affected by actual transmittance of the sample analysed (automatic exposure off).

Most of the digital still cameras in mobile devices rely on automatic exposure control. Generally this feature cannot be deactivated in most devices. Therefore, $I_0$ should be recorded either sequentially or simultaneously to conduct quantitative absorbance measurements. To measure simultaneously, two containers may captured in one image, one filled with 100% transmittance liquid, the other with the sample to be quantified. In most cases pure water can be used as the 100% transmittance liquid.

Liquids Changing Colours Upon Contact with External Substances:

In an embodiment of the method, quantitative analysis of (in general aqueous) solutions, that comprise coloured dissolved species may be performed. In this embodiment, the coloured dissolved species changes its relative contribution to the overall colour of the solution by being chemically converted upon contact with substances added to solution. Numerous chemical reactions are accompanied by a colour change in the visible part of the light spectrum. Chemical mechanisms leading to a colour change include, but are not limited to, redox, acid-base and complexation reactions. Many of these reactions are used routinely, mainly for quantitative chemical analysis of substances external to the coloured aqueous solution (that is, analyzed by adding to coloured aqueous solution) and are evaluated by means of conventional spectrophotometers in the best-suited wavelength range.

If chemical reactions are quantified by absorbance measurements, recording of both the original (unaltered) solution as well as the reaction products is preferable. It is advantageous that there is no longer a need for recording $I_0$, since it can be eliminated arithmetically once both RGB colours of the unaltered solution "blank" and reaction products "sample" are available.

Wavelength-specific molar absorbance of the individual coloured species taking part in the chemical reaction with the substance external to the solution and stoichiometric considerations regarding the interaction coloured solution/external substance may be used for custom calibration. This, in turn, can be used for analysis read-out in form of molar or mass concentrations of the substance added.

In an alternative embodiment, the system can be used for titration. That is, rather than measuring a gradual change in color, an external reagent is added to a solution having a color indicator. The sudden change in color associated with titration is detected by color sensor. In one aspect of this embodiment, the camera is operated in video mode and the external reagent added at a known rate. In this manner, the titration can be operated in real time.

Software:

In an embodiment, software suitable for conducting quantitative absorbance analysis preferably can perform the following sub-tasks:

Image capture (optionally with a built-in camera) or loading of already captured images from device memory.

Cropping of pre-defined pixels containing the relevant colour information.

Calculating average values for the red, green and blue levels leading to single, mean red, green and blue values.

Putting the mean RGB input into a formula node and performing calculations to determine the actual absorbance/concentration.

Analyzing data output (display) and execution of optional data storage operation.

Calculations:

Once mean RGB levels of the cropped area have been calculated, the data may be further processed in the formula node of the software. Further processing may include:

Extraction of species-specific absorption wavelength from RGB emission spectra by means of heuristic principles (R, G and B are supposed to have given emission spectra).

Calculation of light intensities (transmittance) for the sample, and if available, blank or water.

Input of intensity of 0 ($I_0$) from memory, if no sample-specific I0 has been recorded.

If two samples (blank and sample) of a chemical reaction are available, I0 is not relevant.

Calculation of wavelength-specific absorbances using BEER-LAMBERT's law.

Application of a calibration formula (derived from specific molar absorbances) to get molar or mass concentrations of species present in the liquid.

In case of chemical reaction with substance external to the coloured liquid: subtraction and/or addition of blank and sample species concentrations leading to molar or mass concentrations of substance added.

Heuristic methods for extraction of wavelength from average RGB 8-bit levels have been investigated by Dan Bruton at the Department of Physics and Astronomy, Stephen F. Austin State University. However, the RGB spectra provided by Bruton are capped at 256 8-bit levels. This does not match the reality of liquid, coloured species. Therefore, embodiments of the invention include an approach with a graphical extrapolation to (merely theoretical) 8-bit levels beyond 256 to determine the relative contribution (coefficients) of red, green and blue to a selected wavelength.

Wavelength Selection for a Specific Liquid/Dissolved Analyte:

As in conventional colorimetric/visual spectrophotometric practice, the best fitted wavelength for a substance are selected using a full VIS absorption spectrum (ca. 400-700 nm) of the liquid. In some cases, it is advisable not to use one of the absorption maxima of the coloured species. This is to avoid light intensities which re too low at the light-sensor which leads to noise and poor colour rendition.

If multiple, differently coloured species are to be analysed in one single liquid sample, wavelengths should be selected particularly carefully to avoid overlapping ranges of high molar extinction for two or more species. It is generally advisable to select wavelengths, where the expected species show the most significant differences in molar extinction. For each species analysed, at least one suitable wavelength, with minimal interference from other coloured substances should to be selected. This allows the quantitative characterisation of multi-species liquids.

Alternative Methods

The basic setup of the invention includes a light source, a coloured sample with a constant optical path-length, and a colour sensor (e.g., a digital camera). In an alternative embodiment of the method, both the colour sensor and the light source are immersed in the coloured sample. Preferably, the distance (optical path-length) of the emitter (light source) and the detector (camera) are kept constant.

A typical mobile telecommunications device having an integrated digital camera can not be immersed in a liquid. To use such a device, a separate light source, particularly in form of a small white LED, could be shielded in a way that its integrity will not be affected by the surrounding liquid medium.

Experiments have been conducted using fibre-optic cables. The experiments show that both conveyed light intensity as well as camera light sensitivity are sufficient for quantitative absorbance measurement. That is, sufficient light from a remote light source can be transmitted via an optical fibre to the sample such that the light transmitted through the sample to the sensor is sufficient to make quantitative measurements.

In one embodiment, the TFT display of the mobile device itself is used as source of white light. This may be accomplished via fibre-optics. Spectral analysis, however, has revealed that, similar to white LEDs, the full spectrum over the visible range (400-700 nm) is not uniform. This issue may be overcome in another alternative embodiment. This embodiment involves a discontinuous use of the TFT display. In this embodiment, rather than use white light, spectrometrically discrete colours are selected. Preferably, the selected colours are complementary to the absorption maxima of the coloured liquid or dissolved species. In this embodiment, images are displayed in a small portion of the display over short time periods (typically <2 seconds, depending on the camera's ability to capture image sequences). In case of multi-species liquids, several images with different irradiated light spectra (through fibre-optics) may be captured.

EXAMPLES

Example data were generated using a fluorescent light-box, 5 cm (2 inches) optical path-length rectangular glass bottles (two side by side) and an APPLE IPHONE 3G® OS 3.0 with custom software (see Section C.). The colour indicator used was a commercial alkaline colour indicator product (THONHAUSER U.S.A. Inc. TM DESANA MAX, see US Patent Application 2004/0033930 A1) in a 11.8 g/l (3.1 g/gal) aqueous solution at ambient temperature (27° C./81 F).

In a first experiment, the substance external to the aqueous solution was a degassed lager-beer (A-B BUDWEISER, can). The beer was added to the colour solution and reaction with the oxidisers present in the aqueous solution was allowed for 4 minutes. The colour change, induced by a shift in the relative predominance of the three colouring manganese species (oxidation state II, VI and VII, with the respective colours yellow, green and purple) was quantified by capturing a digital image using the built-in camera of the APPLE IPHONE 3G device, analysing the absorbance at 405, 435 and 535 nm and calculating molar concentrations of the three species.

Since the second sample bottle contained an unaltered colour solution (pure purple, manganese VII only), there was no need for acquiring zero intensity ($I_0$). The differences for the three individual manganese species between sample and blank (unaltered) went into the calculation of oxidised organic matter from oxidiser consumption, expressed as [mg/l $CH_2O$].

Two individual samples of APPLE IPHONEs 3G were compared in order to verify inter-device consistency of analytical results. Comparison testing was carried out with simultaneously captured 2 megapixel images from a high-end digital still camera (PANASONIC Corp. LUMIX DMC-LX3, Firmware V1.2), using the best available image quality settings (ISO sensitivity 80, JPEG compression fine).

In another comparison, a smart-phone from a different manufacturer (NOKIA e-SERIES E75) was used for capturing images at the lowest sensitivity (minimal sensor noise) and image sharpening OFF settings.

D.2. Data Evaluation:

The images from the APPLE IPHONEs 3G were analysed in-device using the TM VERIFOX software. Images from the PANASONIC digital still camera and the NOKIA smart-phone were analysed using cropping and image size commands in ADOBE PHOTOSHOP CS3. The mean RGB levels were entered into a MICROSOFT EXCEL spreadsheet containing the identical calculation formulae as the TM VERIFOX software deployed on the APPLE mobile devices.

Figure 6:
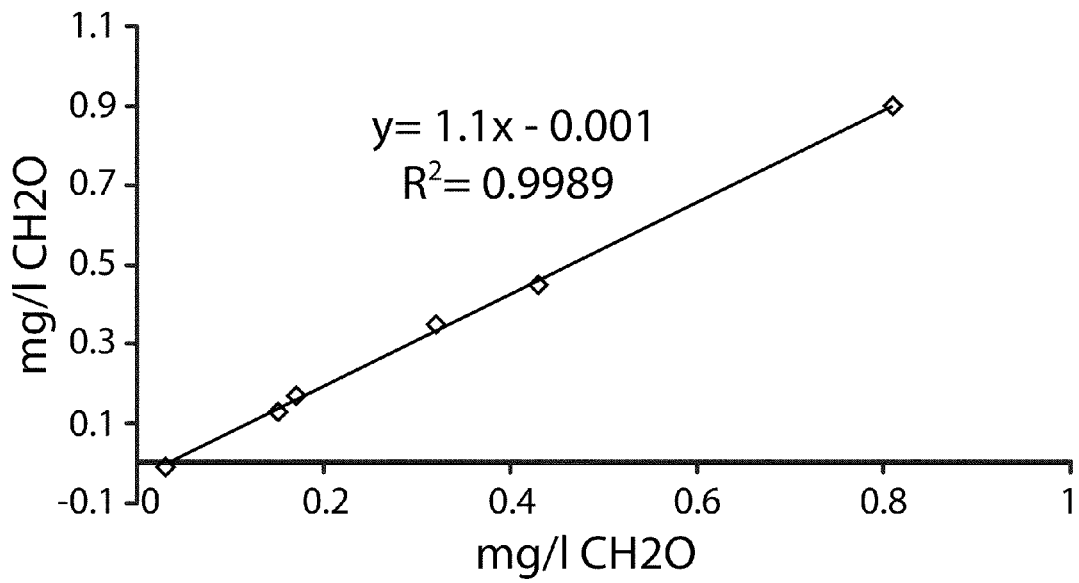
FIG. 6 is a plot illustrating inter-device consistency an embodiment of the invention.

Static Test with Two Individual Devices (Inter-Device):

Tests evaluating the inter-device reliability of the systems and methods of the inventions were conducted and are illustrated in FIG. 6. The tests were conducted by capturing differently coloured aqueous solutions containing various concentrations of organic matter (in this case beer). The varying concentration leads to visually different colours caused by a shift in predominance of manganese species. Two samples of Apple iPhone 3G (Software 3.0) were used and the results were compared. A satisfactory consistency was observed (slope of the scatter-plot was 1.1, with intercept close to zero).

Repeatability Mobile Device and High-End Digital Still Camera (Intra-Device):

Multiple exposures (20 each) of three different concentrations of organic matter (in this case beer), leading to visually different colours caused by shifts in predominance of manganese species, were captured using both an Apple iPhone 3G and a Panasonic Lumix DMC-LX3 digital still camera. The results of these experiments are summarized in the Table below. Neither device was individually calibrated, therefore the data in the table differ from one device to the other. However, a satisfactory repeatability is observed for both devices, with a slight edge in favour of the Apple iPhone 3G smart-phone.

| ml beer added to 100 ml coloured solution: | Apple iPhone 3G arithm. Mean, mg/l CH2O | Apple iPhone 3G std. deviation, mg/l CH2O | Camera Lumix DMC-LX3 arithm. Mean, mg/l CH2O | Camera Lumix DMC-LX3 std. deviation, mg/l CH2O |
|---|---|---|---|---|
| 0.0 | 0.004 | 0.006 | −0.009 | 0.004 |
| 1.0 | 0.44 | 0.012 | 1.13 | 0.085 |
| 8.0 | 1.33 | 0.017 | 1.78 | 0.037 |

Figure 7:
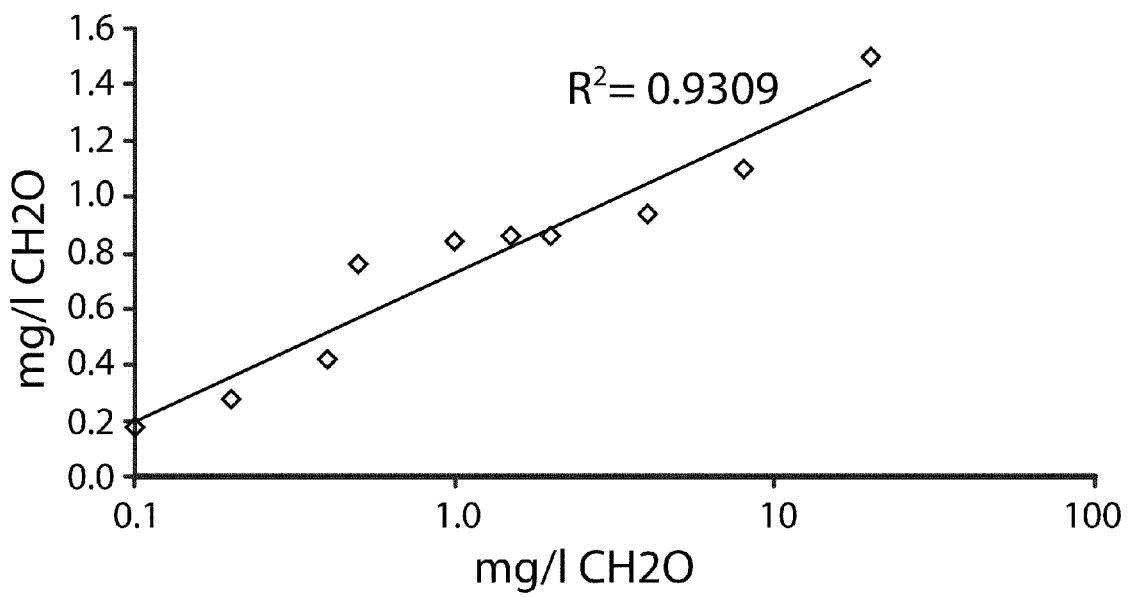
FIG. 7 is a plot illustrating comparing embodiments using different portable devices.

Alternative Device Static Test (NOKIA E75 SYMBIAN S60 $3^{rd}$ Edition Smart-Phone):

Tests evaluating different commercially available portable electronic devices modified to perform absorbance measurements according to embodiments of the invention were conducted and are illustrated in FIG. 7. The tests were conducted by capturing images of differently coloured aqueous solutions containing various concentrations of organic matter (in this case beer), leading to visually different colours caused by shifts in the predominance of manganese species. A Nokia E75 Symbian S60 3rd Edition smart-phone was used. When the results are displayed logarithmically (recommended due to lack of available individual calibration for the device used), a significant and quantitative concentration (ml beer used per 100 ml of coloured solution) dependency of mg/l CH2O read-out can be observed.

The foregoing description of the invention has been presented for purposes of illustration and description. It is not intended to be exhaustive or to limit the invention to the precise form disclosed, and modifications and variations are possible in light of the above teachings or may be acquired from practice of the invention. For instance, the examples were illustrated with aqueous solutions. However, solutions of other solvents such as alcohols may be used. Additionally, the systems and methods may be used on gases, gels, and even semi-transparent coloured solids. The drawings and description were chosen in order to explain the principles of the invention and its practical application. It is intended that the scope of the invention be defined by the claims appended hereto, and their equivalents.

The invention claimed is:

1. A method comprising:
obtaining a mobile electronic device comprising a color sensitive light sensor and outward facing optics;
exposing a sample to light, wherein the sample comprises a colored liquid; and
measuring the amount of light transmitted though a predetermined optical path-length in the sample with the color sensitive light sensor, wherein the sample and the mobile electronic device are not enclosed within the same housing.

2. The method of claim 1, further comprising determining the light absorption of the sample by wavelength-extraction from red, green and blue colors.

3. The method of claim 2, further comprising calculating the mass or molar concentrations of a substance in the sample.

4. The method of claim 1 further comprising adding a color indicating reagent to the sample.

5. The method of claim 1, further comprising adding a reagent of unknown concentration to the sample, the sample comprising a color indicating agent.

6. The method of claim 4, wherein the color indicating reagent is selected from redox, acid-base and complexation.

7. The method of claim 5, wherein the color indicating reagent is selected from redox, acid-base and complexation.

8. The method of claim 1, wherein the color sensitive light sensor is part of a digital camera.

9. The method of claim 1, wherein the mobile electronic device comprises a backlit display and the backlit display is used as the light source.

10. The method of claim 9, wherein the backlit display is used discontinuously by selectively displaying discrete colors for a predetermined amount of time.

11. The method of claim 10, wherein the discrete colors are complementary to absorption maxima of a substance in the sample.

12. The method of claim 9, further comprising channeling light from the backlit display though the sample and to the outward facing optics with an optical fiber.

13. The method of claim 1, wherein the color sensitive light sensor is illuminated uniformly by the light source.

14. The method of claim 1, wherein the mobile electronic device uses 8-bit color processing.

15. The method of claim 1, wherein the light source comprises a source of white light and a source of ultraviolet light.

16. The method of claim 1, further comprising putting the sample in a container having parallel walls.

17. The method of claim 1, wherein the device comprises voice control.

18. The method of claim 1, further comprising measuring the amount of light transmitted though a reference.

19. The method of claim 18, wherein the reference has essentially 100% transmittance.

20. The method of claim 1, wherein if the mobile electronic device has automatic exposure, the automatic exposure is turned off.

21. The method of claim 1, wherein a captured image from the color sensitive light sensor is cropped in a predetermined configuration.

22. The method of claim 1, further comprising determining average values for red, green, and blue light levels.

23. The method of claim 1, wherein the device is configured to capture an image.

24. The method of claim 1, further comprising using a reference transmittance of 100% if no reference transmittance has been measured.

25. The method of claim 1, wherein the mobile electronic device and/or the light source are immersed in the sample.

26. The method of claim 1, wherein the light source is selected from fluorescent and light emitting diode.

27. A mobile electronic device comprising a color sensitive light sensor, a processor, and outward facing optics, the processor comprising computer executable instructions for quantitative analysis of absorbance in a colored liquid, wherein the mobile electronic device is configured to measure the amount of light transmitted though a predetermined optical path-length in the colored liquid with the color sensitive light sensor.

28. The device of claim 27, further comprising a visual or acoustic user interface.

29. The device of claim 27, wherein the device is configured for quantitative analysis of absorbance in the colored liquid with software.

30. The device of claim 27, wherein the device is configured for quantitative analysis of absorbance in the colored liquid with hardware.

31. The device of claim 27, wherein the light sensor is a digital camera.

32. The device of claim 27, wherein the device comprises hardware and firmware and/or software and wherein at least one of the hardware, firmware and software is user-programmable.

33. The device of claim 27, further comprising a user interface comprising a dot-matrix display.

34. The device of claim 27, further comprising a user interface comprising a touch-sensitive display.

35. The device of claim 27, wherein the device is configured to calculate the mean red, green and blue color levels from predetermined portions of the digital image.

36. The device of claim 27, wherein the device is configured to calculate liquid absorbances based on wavelength-extraction of red, green and blue color levels.

37. The device of claim 27, wherein the device is configured to calculate mass or molar concentrations of a substance external to the liquid, further.

38. The device of claim 37, wherein the liquid is reactive towards the substance and changes colors upon contact with the substance.

39. The device of claim 27, further comprising a backlit display configured for use as light source.

40. The device of claim 39, wherein the device is configure to display multiple colors in succession and respective light-sensor intensities are captured.

41. The device of claim 31, wherein the digital camera is configured to operate in video mode.

42. The device of claim 41, wherein the device is configured to monitor a change in color as a function of time.

43. A system comprising:
a mobile electronic device comprising a color sensitive light sensor, a processor, and outward facing optics, the processor comprising computer executable instructions for quantitative analysis of absorbance in a colored liquid; and a light source, wherein the mobile electronic device is configured to measure the amount of light transmitted though a predetermined optical path-length in the colored liquid with the color sensitive light sensor.

44. The system of claim 43, further comprising a fixed optical path length for the colored liquid.

45. A system of claim 43, further comprising a fluorescent lamp as light source.

46. The system of claim 43, further comprising a user interface physically built into the mobile device.

47. The system of claim 43, wherein the mobile electronic device comprises a backlit display configured for use as light source.

48. The system of claim 47, further comprising an optical fiber configured to transmit light from the backlit display to the colored liquid.

49. The system of claim 48, further comprising an optical fiber configured to transmit light from the colored liquid to the color sensitive light sensor.

50. The system of claim 43, wherein the mobile electronic device is configured to determine light absorption of the colored liquid based on wavelength-extraction from red, green and blue colors.

51. The system of claim 50, wherein the mobile electronic device is configured to calculate the mass or molar concentrations of a substance in the colored liquid.

52. The system of claim 43, wherein the color sensitive light sensor is part of a digital camera.

53. The system of claim 43, wherein the mobile electronic device is configured to use 8-bit color processing.

54. The system of claim 43, further comprising a sample and a blank.

55. The system of claim 54, wherein the sample is selected from liquids, gases, gels, and semi-transparent solids.

* * * * *